(12) United States Patent
Glenn et al.

(10) Patent No.: US 11,558,701 B2
(45) Date of Patent: Jan. 17, 2023

(54) ELECTRODES FOR HEARING DEVICES AND RELATED METHODS

(71) Applicant: Starkey Laboratories, Inc., Eden Prairie, MN (US)

(72) Inventors: Janet Marie Glenn, Coon Rapids, MN (US); Mark T. Farley, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 89 days.

(21) Appl. No.: 16/158,664

(22) Filed: Oct. 12, 2018

(65) Prior Publication Data
US 2019/0111261 A1    Apr. 18, 2019

Related U.S. Application Data

(60) Provisional application No. 62/573,039, filed on Oct. 16, 2017.

(51) Int. Cl.
*B33Y 80/00*    (2015.01)
*H04R 25/00*    (2006.01)
(Continued)

(52) U.S. Cl.
CPC ........... *H04R 25/652* (2013.01); *A61B 5/291* (2021.01); *A61B 5/6817* (2013.01);
(Continued)

(58) Field of Classification Search
CPC .. A61N 1/36036; A61N 1/0472; B33Y 80/00; B33Y 10/00; A61B 5/0478;
(Continued)

(56) References Cited

U.S. PATENT DOCUMENTS 4,324,680 A * 4/1982 Kubota ................. H01M 4/582
429/219
4,819,647 A * 4/1989 Byers ................... A61N 1/0541
607/116

(Continued)

FOREIGN PATENT DOCUMENTS

EP    0084973 A2    8/1983
EP    2545719 B1    11/2013
(Continued)

OTHER PUBLICATIONS

Fiedler et al., "Novel TiN-based dry EEG electrodes: Influence of electrode shape and number on contact impedance and signal quality," *IFMBE Proceedings*, Dec. 2009, 5 pages.

(Continued)

*Primary Examiner* — Ankit D Tejani
*Assistant Examiner* — Joshua Brendon Solomon
(74) *Attorney, Agent, or Firm* — Mueting Raasch Group

(57) ABSTRACT

A hearing device for electrically coupling to skin of a user includes a body having a housing forming at least part of an outer surface. The device includes an acoustic transducer and an electrode disposed at least partially in the body. The electrode includes an outer conductor disposed at least partially in the housing and an inner conductor electrically coupled to the outer conductor and disposed subflush to the outer surface. A method of forming the hearing device includes providing a cast shell, forming an elastomeric conductor in a cavity of the cast shell, and removing a thin outer wall of the cast shell to form the housing of the hearing device.

19 Claims, 7 Drawing Sheets

(51) Int. Cl.
*A61N 1/36* (2006.01)
*A61N 1/04* (2006.01)
*A61B 5/00* (2006.01)
*A61B 5/291* (2021.01)
*B33Y 10/00* (2015.01)
*H04R 1/10* (2006.01)

(52) U.S. Cl.
CPC ....... *A61N 1/0472* (2013.01); *A61N 1/36036* (2017.08); *B33Y 80/00* (2014.12); *H04R 25/658* (2013.01); *B33Y 10/00* (2014.12); *H04R 1/1016* (2013.01); *H04R 1/1041* (2013.01); *H04R 1/1058* (2013.01); *H04R 2225/025* (2013.01); *H04R 2225/61* (2013.01)

(58) Field of Classification Search
CPC .. A61B 5/6817; H04R 25/652; H04R 25/658; H04R 1/1016; H04R 1/1041; H04R 1/1058; H04R 2225/025; H04R 2225/61
See application file for complete search history.

(56) References Cited

U.S. PATENT DOCUMENTS

| | | | | |
|---|---|---|---|---|
| 5,571,148 | A * | 11/1996 | Loeb | A61N 1/36038 607/57 |
| 5,712,917 | A * | 1/1998 | Offutt | H04R 25/606 381/151 |
| 8,880,193 | B1 * | 11/2014 | Thenuwara | A61N 1/0541 607/137 |
| 8,884,767 | B2 | 11/2014 | Kidmose | |
| 8,923,542 | B2 | 12/2014 | Kilsgaard et al. | |
| 9,025,800 | B2 | 5/2015 | Kidmose et al. | |
| 2006/0183965 | A1 * | 8/2006 | Kasic | A61N 1/36036 600/25 |
| 2008/0177353 | A1 * | 7/2008 | Hirota | A61N 1/36036 607/57 |
| 2012/0155684 | A1 * | 6/2012 | De Finis | H04R 25/60 381/322 |
| 2012/0209101 | A1 * | 8/2012 | Kidmose | H04R 25/652 29/874 |
| 2014/0163626 | A1 * | 6/2014 | Walling | A61N 1/375 607/2 |
| 2016/0317352 | A1 | 11/2016 | Blumer et al. | |
| 2017/0099553 | A1 | 4/2017 | Sacha et al. | |
| 2017/0180882 | A1 | 6/2017 | Lunner et al. | |
| 2017/0340232 | A1 * | 11/2017 | Stewart | A61B 5/0408 |
| 2017/0360614 | A1 * | 12/2017 | Ely | H04R 1/1016 |
| 2018/0117310 | A1 * | 5/2018 | Sibary | A61N 1/36036 |
| 2018/0206788 | A1 * | 7/2018 | Andersen | A61B 5/6847 |
| 2018/0234781 | A1 | 8/2018 | Stewart et al. | |
| 2019/0014426 | A1 * | 1/2019 | Karamuk | H04R 25/602 |

FOREIGN PATENT DOCUMENTS

| | | | | |
|---|---|---|---|---|
| EP | | 2454892 B1 | 3/2015 | |
| EP | | 2986031 A1 | 2/2016 | |
| WO | WO 2011/000383 A1 | | 1/2011 | |
| WO | WO 2017/054875 A1 | | 4/2017 | |
| WO | WO-2017054875 A1 * | | 4/2017 | ............. A61B 5/291 |

OTHER PUBLICATIONS

Fonseca et al., "A Novel Dry Active Electrode for EEG Recording," *IEEE Transactions on Biomedical Engineering*, Jan. 2007; 54(1):162-165.

International Search Report and Written Opinion for Application No. PCT/US2018/054298, dated Jan. 31, 2019, 13 pages.

Manabe et al., "Conductive Rubber Electrodes for Earphone-Based Eye Gesture Input Interface," *Personal and Ubiquitous Computing*, Jan. 2015, 19(1):143-154.

Norton et al., "Soft, Curved Electrode System Capable of Integration on the Auricle as a Persistent Brain-Computer Interface," *PNAS*, Mar. 31, 2015; 112(13):3920-3925.

Toyama et al., "A non-adhesive solid-gel electrode for non-invasive brain-machine interface," *Frontiers in Neurology*, Jul. 18, 2012; vol. 3, Article 114, 8 pages.

* cited by examiner

ELECTRODES FOR HEARING DEVICES AND RELATED METHODS

CROSS-REFERENCE TO RELATED APPLICATIONS

The present disclosure claims the benefit of U.S. Provisional Patent Application No. 62/573,039, filed Oct. 16, 2017, entitled ELECTRODES FOR HEARING DEVICES AND RELATED METHODS, which is incorporated entirely herein by reference.

FIELD

The present disclosure relates to electrodes. In particular, the present disclosure relates to an electrode for a hearing device that electrically couples to skin of a user.

BACKGROUND

Hearing devices may include hearing aids or a device with a transducer for providing personalized sound to a user's ear. Hearing aids can be used to assist patients suffering hearing loss by transmitting amplified sounds to one or both ear canals. Such devices typically include hearing assistance components, such as a microphone for receiving ambient sound, an amplifier for amplifying the microphone signal in a manner that depends upon the frequency and amplitude of the microphone signal, a speaker or receiver for converting the amplified microphone signal to sound for the wearer, and a battery for powering the components.

In certain types of hearing aids, the hearing assistance components are enclosed by a housing that is designed to be worn in the ear for both aesthetic and functional reasons. Such devices may be referred to as in-the-ear (ITE), in-the-canal (ITC), completely-in-the-canal (CIC) type, or invisible-in-the-canal (IIC) hearing assistance devices. Other types of devices, referred to as receiver-in-canal (RIC) devices, include a receiver housing that is worn in the ear. A portion of the RIC devices may be worn outside of the ear.

It is well known to use electrodes on skin of a patient to monitor one or more conditions. Such electrodes have been used, for example, in a skull cap for brain computer interface (BCI) applications, such as electroencephalography (EEG) or electrooculography (EOG). Such BCI applications may require electrodes that can provide precise electrical measurements of electrical signals present on the skin.

Some existing electrodes may be described as "wet" electrodes and may require an electrolytic liquid, which may be incorporated into a gel, to be placed between the electrode and the skin before each use. The electrolytic liquid may be consumed after each use of the wet electrode. Further, the sensation of electrolytic liquid against the skin may be uncomfortable to many users, particularly on skin areas sensitive to moisture such as the ear canal.

Other existing electrodes may be described as "dry" electrodes, which may not require an electrical coupling gel. However, many dry electrodes require harsh cleaning to prepare the skin before electrode replacement, as well as a significant force to be applied on the skin to establish electrical coupling. Further, dry electrodes may be susceptible to signal drift over time due, for example, to material degradation.

The limitations of existing wet and dry electrodes may be tolerable in a clinical setting for short periods of use. But over extended periods of use, particularly outside of the clinic in many daily wear applications, these limitations may render existing wet and dry electrodes unsuitable, particularly for use in a hearing device.

SUMMARY

Various aspects of the present disclosure relate to a hearing device including an electrode for electrically coupling to the skin of a user. The hearing device may include a body having a housing and hearing device components. The electrode may be electrically coupled to one or more hearing device components disposed in the body. The electrode may facilitate electrical coupling to skin of a user and may be used as a dry or wet electrode, for example, by utilizing conductive materials or structural designs that provide comfort, good electrical conductivity with the skin, and mitigation of signal drift over time.

In one aspect, the present disclosure relates to a hearing device for electrically coupling to skin of a user. The device includes a body comprising a housing forming at least part of an outer surface. The device also includes an acoustic transducer disposed at least partially in the body. The device further includes an electrode disposed at least partially in the body. The electrode has an outer conductor disposed at least partially in the housing and forming at least part of the outer surface. The electrode also has an inner conductor electrically coupled to the outer conductor and disposed subflush to the outer surface.

In another aspect, the present disclosure relates to a method of making a hearing device comprising a housing and an electrode configured to electrically couple to skin of a user. The method includes providing a cast shell comprising a thin outer wall, a thick outer wall, an inner wall between the thin and thick outer walls, a cavity proximate to the thin outer wall, and a void proximate to the thick outer wall separated from the cavity by the inner wall. The method also includes forming an elastomeric conductor in the cavity of the cast shell. The method further includes removing the thin outer wall to form the housing comprising an outer surface defined at least partially by the thick outer wall and the elastomeric conductor.

In another aspect, the present disclosure relates to a method of making a hearing device comprising a housing and an electrode configured to electrically couple to skin of a user. The method includes forming a shell of the housing, forming a frame of the housing, and disposing at least one hearing device component on the frame. The method also includes inserting the frame into the shell and electrically coupling the electrode to the at least one hearing device component. The electrode is disposed at least partially in the shell.

The disclosure may be more completely understood in consideration of the following detailed description of various embodiments of the disclosure in connection with the accompanying drawings.

DETAILED DESCRIPTION

This disclosure relates to electrodes to facilitate electrical coupling to skin of a user. Although reference is made herein to electrodes for a hearing device used in BCI applications, electrodes of this disclosure may be used with any device or application in which electrical coupling to the skin may be desirable. In general, non-limiting examples of devices include hearing aids, hearable devices (for example, earbuds, Bluetooth headsets, or back-vented vented tweeter-woofer devices), wearables or health monitors (for example, step counter or heartrate monitor), or other portable or personal electronics (for example, smartwatch or smartphone). Various other applications will become apparent to one of skill in the art having the benefit of the present disclosure.

It may be desirable to provide an electrode that electrically couples to the skin of the user to facilitate taking precise measurements, which may be desirable in BCI applications. It may also be desirable for the electrode to be capable of use as a dry electrode that is convenient for repeatable use and does not require an electrolytic liquid to achieve precise measurements. Further, it may be desirable to establish electrical coupling between the electrode and the skin without uncomfortable amounts of pressure being applied to the ear canal.

The present disclosure provides an electrode for a hearing device to electrically couple to skin of a user. The hearing device may include a body having a housing and an acoustic transducer disposed at least partially or entirely in the body. The housing may be partially soft, hard, or contoured to facilitate comfortable use. The electrode may include an outer conductor and an inner conductor. The electrode may be electrically coupled to one or more hearing device components disposed in the body, for example, using the inner conductor. The hearing device including the electrode may be formed using a variety of methods to produce different types of electrodes that may be suitable for use in various BCI applications, such as EEG (which may benefit from larger electrodes) or EOG (which may benefit from smaller electrodes). The electrode may include various features, such as microfeatures or electrolytic liquid, to provide a good electrical coupling to the skin (for example, low SNR and few artifacts) without significant pressure being applied to the skin. The electrode may be used as a dry electrode which may facilitate comfortable daily use in non-clinical settings. In particular, the electrode may be suitable for repeated use without the need for adding an electrolytic liquid or other frequent maintenance of the electrode. The electrode may also be used as wet electrode, which may provide an even better electrical coupling to the skin. The hearing device may be used in an environment including a user as shown in FIG. 1 and FIG. 2.

Figure 1:
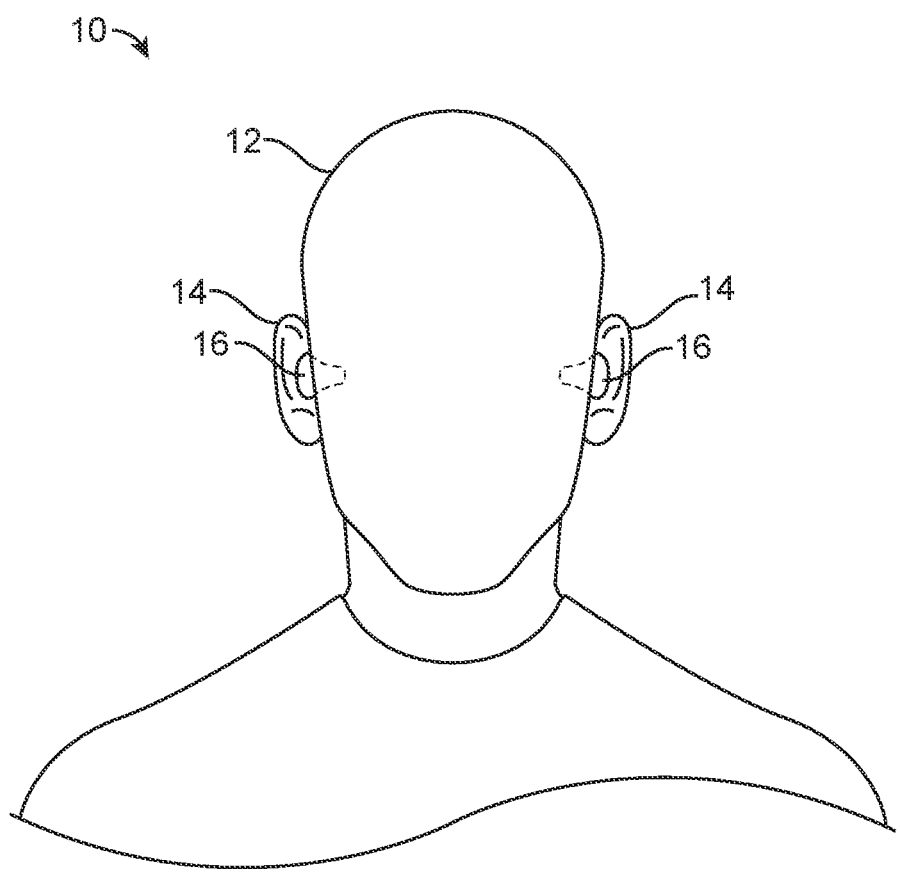
FIG. 1 is an illustration of an environment including a user of a hearing device.
Figure 2:
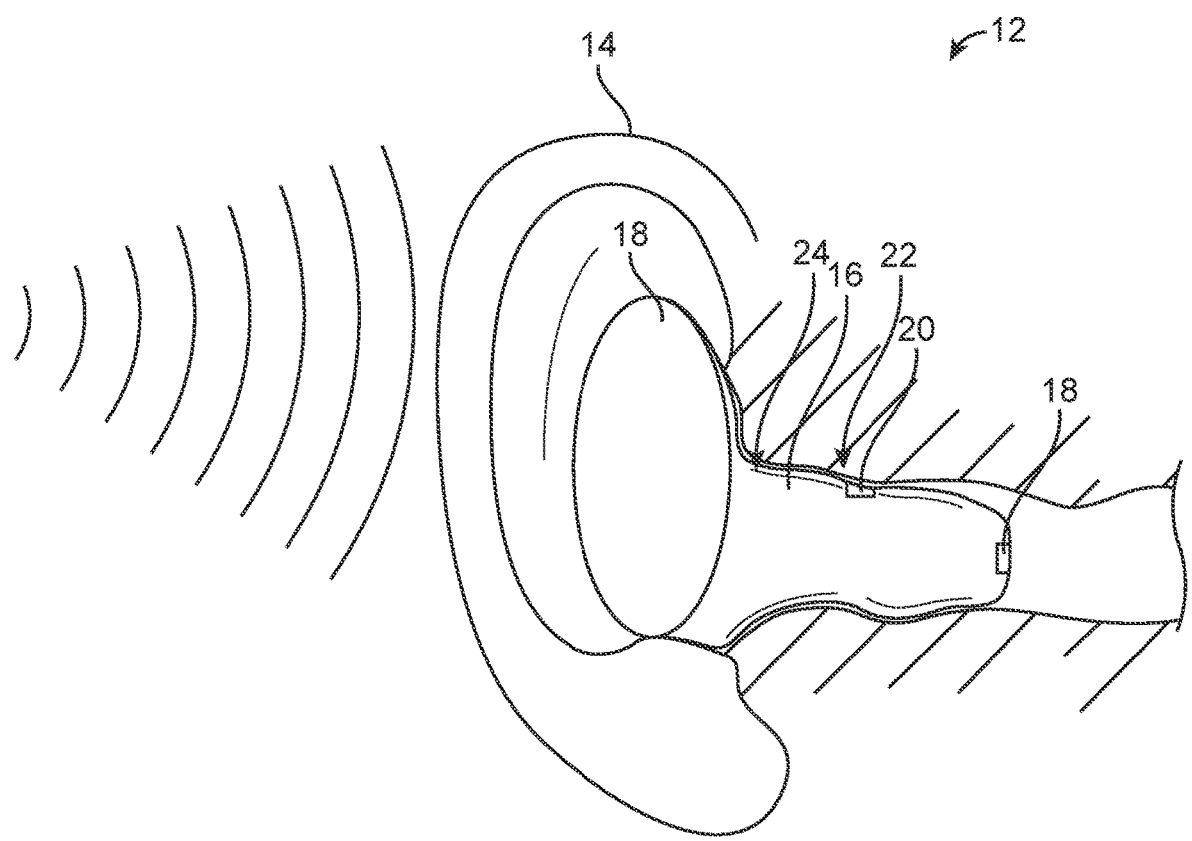
FIG. 2 is an illustration of the hearing device of FIG. 1 used in the ear of the user.

As shown in FIG. 1, a hearing device 16 may be used in an environment 10 and, in particular, used in the ears 14 of a user 12. For example, one or more hearing devices 16 may be disposed at least partially in the ear canal of each ear 14. The hearing device 16 may be a hearing aid. As shown in FIG. 2, the hearing device 16 may include one or more acoustic transducers 18. Sound may approach the ear 14 of the user 12 and be received by a receiving acoustic transducer 18 (for example, a microphone), which may be positioned to collect sound from the external environment. The sound received may be modulated and transmitted toward an ear drum of the ear 14 using a transmitting acoustic transducer 18 (for example, a speaker/receiver), which may be on an opposite end of the hearing device 16 from the transmitting acoustic transducer.

The hearing device 16 may include an electrode 20 and an outer surface 24. One or both of the electrode 20 and the outer surface 24 may be disposed proximate or adjacent to the skin 22 of the user 12 when the hearing device 16 is in use. The electrode 20 may be disposed subflush, flush, or superflush to the outer surface 24. In some embodiments, the electrode 20 may be disposed between the receiving and transmitting acoustic transducers 18.

A hearing device 16 typically includes at least one enclosure or housing and one or more hearing device components, such as one or more transducers 18 (for example, a speaker/receiver and a microphone), hearing device electronics including processing electronics, and a power source (for example, a battery). In one or more embodiments, the battery may be rechargeable. In one or more embodiments, multiple energy sources may be employed. The housing of the hearing device 16 may be custom made to fit the contours of the user's skin, such as skin in the ear canal, to increase comfort over extended periods of being worn. In some embodiments, one or more transducers may be optional (for example, the microphone may be optional). In some embodiments, the hearing device electronics may include a communication interface (for example, which may include an antenna) to communicate with one or more remote devices (for example, a smartphone, tablet, or other hearing device).

The electrode 20 may provide a "good" electrical signal to the electronics in the hearing device 16 that is sufficient for use in BCI applications, such as EEG or EOG. In some applications, a "good" electrical signal may be defined quantitatively in terms of an SNR within the range of a skull cap having about 96 electrodes. In some embodiments, the electrodes 20 of the hearing device 16 may be suited to detect frequency bands useful for one or more applications. For example, the electrodes 20 of the hearing device 16 may detect brain waves, such as alpha waves (about 7.5 Hz to about 12.5 Hz) and delta waves (about 0.5 Hz to about 4 Hz).

The electrode 20 may be capable of establishing "good" electrical contact with a minimal, or at least acceptable, amount of surface fatigue to the ear. The surface fatigue to the ear may be defined as a measure of user discomfort. In some embodiments, particularly in which the device 16 is custom fit to the user's ear, the design of the device 16 may define an ear deformation depth or ear deformation protrusion, which may be defined as the distance that the device is designed to deform the surface of the user's ear at a particular location when the device is inserted into the ear as compared to when the ear has no device therein. In general, a greater the ear deformation depth or ear deformation protrusion may facilitate a more secure fitting of the device 16 to the user's ear but may also be more likely to cause surface fatigue. On the other hand, too small of an ear deformation depth or ear deformation protrusion may result in poor electrical contact with the skin of the ear for BCI application measurements. In some embodiments, to provide good electrical contact while providing acceptable surface fatigue, the ear deformation depth or ear deformation protrusion may be defined as being less than or equal to about 3 mm, about 2 mm, about 1.5 mm, or about 1 mm.

Figure 3:
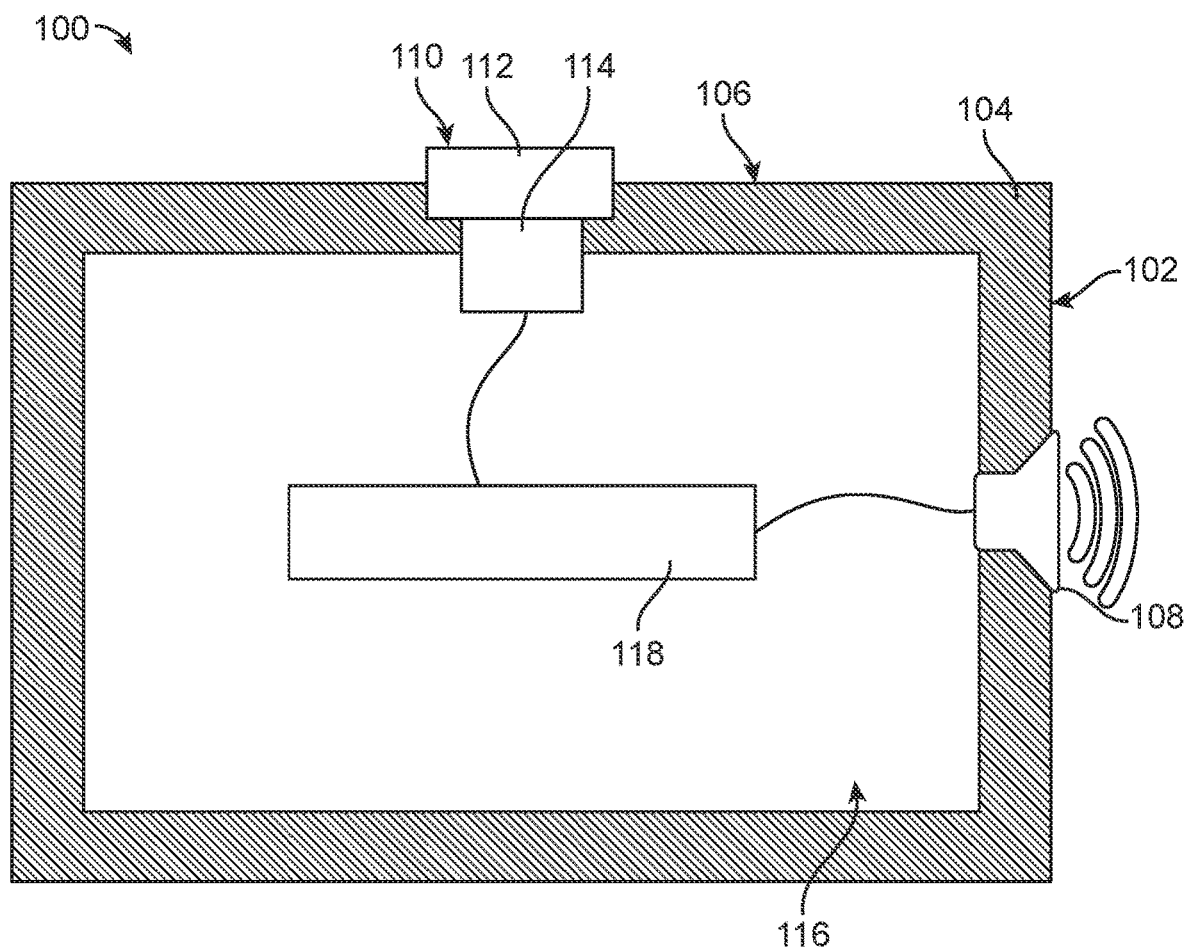
FIG. 3 is a diagram view of the hearing device of FIG. 1 showing various components.

FIG. 3 shows a hearing device 100 that may be used to electrically couple to the skin of a user in a diagram view. The hearing device 100 may include a body 102 having a housing 104. In some embodiments, the housing 104 may be formed of any suitable biocompatible material, which may be, for example, a polymer material.

The housing 104 may form at least part or all of an outer surface 106 of the hearing device 100. In some embodiments, the outer surface 106 may be described as an outermost surface of the hearing device 100. The hearing device 100 may include an acoustic transducer 108. The acoustic transducer 108 may be disposed at least partially in the housing 104 of the body 102. The acoustic transducer 108 may form at least part of the outer surface 106. In some embodiments, the acoustic transducer 108 may be recessed from the outer surface 106 (for example, disposed subflush to the outer surface) and be in acoustic communication with the external environment by an aperture formed in the housing 104 of the hearing device 100. Preferably, at least one acoustic transducer 108 is acoustically coupled with the external environment to receive sound.

The hearing device 100 includes one or more electrodes 110. In some embodiments, the hearing device 100 may include a plurality of electrodes 110. An electrical signal may be measured using the electrode 110, for example, between two or more electrodes 110 of the same hearing device 100, between two hearing devices (for example, one in each ear), or between a hearing device and another device having an electrode (for example, an electrode of a scalp cap).

The electrode 110 may include an outer conductor 112 and an inner conductor 114. In one manner of characterization, the outer conductor 112 is disposed closer to the external environment than the inner conductor 114. The inner conductor 114 may be electrically coupled to the outer conductor 112. The outer conductor 112 or the inner conductor 114 may form at least part of the outer surface 106 of the hearing device 100. The outer conductor 112 or the inner conductor 114 may be disposed at least partially or entirely in the housing 104 or the body 102.

One electrode 110 of the hearing device 100 may be the same size as or a different size than another electrode 110 of the same hearing device 100. In some embodiments, the size of the electrode 110 or any of its components, such as the conductors 112, 114, may be specifically sized to be suitable for particular applications as described herein in more detail, particularly as a trade off to the spacing between electrodes.

The outer conductor 112 may be the same size as or a different size than the inner conductor 114. The size of the conductors 112, 114 may be defined in terms of outer surface area, total volume, conductivity/resistance, or other characteristics that may affect electrical coupling, particularly to the skin.

The electrode 110 or any of its components, such as conductors 112, 114, may be disposed at least partially or entirely in the housing 104 or the body 102 of the hearing device 100. The electrode 110 may be described as being superflush to the housing 104 when an outer portion of the electrode extends beyond the housing. The electrode 110 may be described as being flush to the housing 104 when the outer portion of the electrode extends about even with the housing. The electrode 110 may be described as being subflush to the housing 104 when an outer portion of the electrode is recessed in the housing 104.

In some embodiments, to provide good electrical contact with acceptable surface fatigue, a superflush electrode 110 may protrude from the housing 104 to define a convex protrusion height less than or equal to about 3 mm, about 2 mm, about 1.5 mm, or about 1 mm. In some embodiments, a subflush electrode 110 may recess from the housing 104 to define a concave recess depth less than or equal to about 2 mm, about 1.5 mm, about 1 mm, or about 0.5 mm.

The outer conductor 112 or the inner conductor 114 may be described individually as being subflush, flush, or superflush to the outer surface 106, the housing 104, or the body 102. For example, in some embodiments, the outer conductor 112 may be disposed superflush to the housing 104 and define at least part of the outer surface 106, and the inner conductor 114 may be disposed subflush to the outer surface 106. In other embodiments, the outer conductor 112 may be disposed subflush to the housing 104. In still other embodiments, the outer conductor 112 may be disposed flush to the housing 104 and entirely disposed within the housing.

The body 102 may include a void 116 interior to the housing 104. The void 116 may be defined at least partially by the housing 104. One or more hearing device components 118 may be disposed at least partially or entirely in the void 116. The acoustic transducer 108 may be disposed at least partially or entirely in the void 116. The electrode 110 or any of its components, such as conductors 112, 114, may be disposed at least partially or entirely in the void 116.

The electrode 110 may be directly couplable to the skin of the user to provide good electrical coupling. In some embodiments, the electrode 110 may be flush or superflush to facilitate direct coupling to the skin. For example, the outer conductor 112 may be disposed at least partially in a cavity, which may be defined at least partially by a subflush inner conductor 114. The outer conductor 112 may rest on an outer surface of the inner conductor 114. Direct coupling may facilitate ease of use because, for example, an electrolytic liquid may not need to be added each time the user puts on the hearing device 100.

In some embodiments, however, the electrode 110 or any of its components, such as the conductors 112, 114, may include or be formed at least partially of an electrolytic liquid. Although an electrolytic liquid may not be necessary, using the liquid may facilitate good electrical coupling and be suitable for at least some applications.

The electrode 110 may also be indirectly couplable to the skin of the user to provide good electrical coupling. Preferably, in some embodiments, the electrode 110 or any of its components, such as the conductors 112, 114, may be subflush to the housing 104 to form a cavity to hold an electrolytic liquid, which may be in the form of an electrolytic gel. A gel may hold its shape while retaining the electrolytic liquid. The formation of the cavity may facilitate retaining the electrolytic gel proximate or adjacent to the electrode 110 and may mitigate the uncomfortable feeling of liquid against the skin by restraining the liquid to a limited surface area.

The electrode 110 or any of its components, such as the conductors 112, 114, may be formed of any suitable conductive material. A suitable conductive material may be at least partially or entirely compressible (for example, soft) or at least partially or entirely incompressible (for example, hard). A compressible conductive material may provide a rebound force, which may facilitate electrical coupling. In some embodiments, an outer portion of the electrode 110, such as the outer conductor 112, may be formed of a compressible conductive material. A compressible conductive material used in an outer portion of the electrode 110 may facilitate comfort. An incompressible conductive material used in an outer portion of the electrode 110 may facilitate ease of manual handling and cleaning.

The electrode 110 may be at least partially solid or at least partially liquid. Non-limiting examples of suitable conductive material for conductors 112, 114 of the electrode 110 include one or more of gold, stainless steel, aluminum, titanium, titanium nitride, silver, silver chloride, silver-silver chloride, graphene, and electrolytic liquid (for example, in the form of a gel). In some embodiments, preferably, a superflush electrode 110 may be made of gold or a composite material containing gold. In some embodiments, preferably, a subflush electrode 110 may be made of silver-silver chloride or a composite material containing one or more of silver and silver chloride. An electrolytic liquid may be disposed on the subflush electrode 110. In some embodiments, the electrode 110 may include a material capable of absorbing an electrolytic liquid to provide electrical conduction. The material may be "recharged" using electrolytic liquid. Also, such an absorptive material may become more conductive in response to absorbing the user's own perspiration or ear wax.

In some embodiments, the electrode 110 may include solid outer and inner conductors 112, 114. An electrolytic liquid may be further disposed between the outer conductor 112 and the skin of the user. Preferably, in some embodiments, the electrode 110 does not include any liquid exposed to the skin of the user. In some embodiments, the electrode 110 may include a liquid outer conductor 112 and a solid inner conductor 114. For example, the outer conductor 112 may be formed at least partially or entirely of a liquid (for example, an electrolytic gel) and the inner conductor 114 may be solid.

The electrode 110 or any of its components, such as conductors 112, 114, may include an elastomer. In some embodiments, a conductive material may be embedded or disposed in an elastomer to provide electrical conductivity through the thickness of the elastomer. The resulting material may be described as an elastomeric conductor or a conductive elastomer. The embedded conductive material may be powdered or chopped. Preferably, in some embodiments, the conductive material may be powdered and include one or more of silver, silver chloride, and silver-silver nitride. Preferably, in some embodiments, the conductive material may be chopped and include one or more of titanium and titanium nitride.

As used herein, "chopped" material may refer to coarse grains of material, for example, in the micrometer range, whereas "powdered" material may refer to fine grains of material, for example, in the nanometer range. For example, chopped material may be within range no less than about 0.1 micrometers, about 0.5 micrometers, or about 1 micrometer to no more than about 1000 micrometers, about 500 micrometers, or about 100 micrometers.

The electrode 110 or any of its components, such as conductors 112, 114, may include printed conductive material. For example, conductive material may be printed on an insulating material or other conductive material. In some embodiments, conductive material may be printed on a surface of an insulating elastomer to form the outer conductor 112. The inner conductor 114 may extend through an insulating elastomer of the housing 104 to electrically couple to a printed outer conductor 112. In some embodiments, conductive material may be printed on a surface of the inner conductor 114.

The electrode 110 or any of its components, such as conductors 112, 114, may be integrally formed with at least a portion of the housing 104. In some embodiments, the electrode 110 may include an elastomer integrally formed with an insulating elastomer of the housing 104. For example, a portion of an elastomer may be embedded with conductive material to form the electrode 110 and remaining portions of the elastomer are not embedded with conductive material to form an insulating portion of the housing 104. In some embodiments, the electrode 110 may be described as part of the housing 104.

The electrode 110 or any of its components, such as conductors 112, 114, may be formed by additive manufacturing processes. Non-limiting examples of additive manufacturing processes include one or more of 3D printing and electroplating. Non-limiting examples of 3D printing include one or more of cold-press sintering, direct metal laser sintering (DMLS), and fused deposition modeling (FDM). Preferably, in some embodiments, the electrode 110 or any of its components, such as conductors 112, 114, may be formed at least partially or entirely using 3D printing.

In some embodiments, the electrode 110 or any of its components, such as conductors 112, 114, may be formed by negative manufacturing processes, such as masked lithography. For example, the housing 104 may be formed and then a portion may be removed to make room for the electrode 110.

The electrode 110 or any of its components, such as conductors 112, 114, may be removably coupled to the housing 104, body 102, or other components of the electrode 110 (for example, including being removably disposed in a cavity of the housing). In some embodiments, the electrode 110 or any of its components, such as the conductors 112, 114, may be replaceable or disposable, for example, upon being worn out or soiled. Being removable may facilitate easy replacement of the electrode 110 or any of its components. For example, in some embodiments, the outer conductor 112 may be removably coupled to the inner conductor 114, which may be removably or permanently coupled to the housing 104. The outer conductor 112 may be easily replaceable.

The electrode 110 or any of its components, such as conductors 112, 114, may include a pellet including powdered conductive material. As used herein, a "pellet" refers to compacted or pressed material, such as powdered conductive material compacted together to form a generally cylindrical pellet or any other suitable shape that allows electrical conduction through the pellet.

The pellet may be formed using any suitable technique. In some embodiments, the pellet may be formed using sintering, which is a process of compacting and forming a solid mass of material by heat or pressure without melting it to the point of liquefaction. In some embodiments, the outer conductor 112 of the electrode 110 may include the textured axial surface of the pellet. For a pellet shaped like a cylinder, an axial surface of the pellet may be coarser or more textured than the radial surface of the pellet. Axial loading during the sintering process along the length of the cylindrical pellet may be lower (for example, in terms of pounds per square inch or psi) than the radial loading, which may result in a coarser axial surface compared to the radial surface of the pellet. Although both surfaces may appear to be smooth to the naked eye, the axial surface may be coarser or textured compared to the radial surface, for example, at the micrometer level.

In some embodiments, the outer surface of the electrode 110 may be described as smooth. The smooth outer surface may be formed of any suitable technique, such as sintering with high axial loading or any suitable plating process.

In general, particularly in the absence of an electrolytic gel, a textured outer surface of the electrode 110 may provide a better electrical interface to skin when compared to a smooth surface of the electrode. In some embodiments, an electrolytic gel may be disposed on the outer surface of the electrode 110 to facilitate electrical coupling to the skin, whether the outer surface is textured or smooth. For example, an electrolytic gel may facilitate electrical coupling between the outer surface of the outer conductor 112 of the electrode 110 and the user's skin.

The electrode 110 or any of its components, such as conductors 112, 114, may have a microtextured, or micro-pitted, outer surface. As used herein, a "microtextured" or "micro-pitted" refers to a microfeature measuring in the micrometer range (for example, as low as about 0.001 micrometers, or as low as about 1 micrometer, to as high as about 999 micrometers, or as high as about 500 micrometers) that is present at least partially or entirely across the surface. An outer surface with such microfeatures may facilitate good electrical coupling to the skin with a direct interface. The effectiveness of the microfeatures to may depend on, for example, parameters of the sintering process, such as axial loading, of the conductive material particles used to form the outer conductor 112 of the electrode 110.

In some embodiments, an outer portion of the electrode 110 or any of its components, such as conductors 112, 114, may be formed using a plating process. The plated electrode 110 may be formed to match or almost match the outer contour of the housing 104, which may be preferably convex. In some embodiments, compared to a cylindrical pellet, a contoured plated electrode 110 may provide a better fit and contact area with the ear of the user. The plated electrode 110 may be formed of any suitable material, such as an implant grade metal. In some embodiments, the plated electrode 110 includes gold or is formed of a composite material containing gold.

An outer portion of the electrode 110 or any of its components, such as conductors 112, 114, may be formed of one or more materials capable of withstanding exposure to the skin of the user and to the ambient environment on a regular basis. To provide a precise electrical measurement over an expected lifetime of the outer conductor 112 of the hearing device 100 (for example, without significant signal drift over time), such materials may be biocompatible and resistant to corrosion or degradation. Degradation may be caused by, for example, oxidation due to exposure to perspiration from the skin and earwax in the ear canal. Preferably, in some embodiments, an outer portion of the electrode 110, such as the outer conductor 112, may include one or more of silver-silver chloride and titanium nitride.

Hearing device components 118 may include one or more of the acoustic transducer 108 and the electrode 110. The acoustic transducer 108 and the electrode 110 may be operatively coupled to other hearing device components 118 of the hearing device 100. In some embodiments, the electrode 110 may be coupled using wire conductors. For example, the inner conductor 114 may include a wire conductor that is electrically coupled to the outer conductor 112.

Hearing device components 118 may include a controller, which may carry out various functionality of the hearing device 100, such as taking measurements with the electrodes. Measurements of electrical signals using the electrode 110 may be further processed in the hearing device 100 or may be transmitted using a communication interface (for example, an antenna) to other devices or equipment for further processing.

In addition to measuring, such as for BCI applications, the electrode 110 may be used for other functionality of the hearing device 100. For example, the controller may be used to carry out hearing aid functionality, which may involve using the acoustic transducer 108. As another example, the controller may be used for power savings of the hearing device 100. When the controller detects a signal using the electrode 110, the hearing device 100 may turn on. When the controller detects no signal using the electrode 110, the hearing device 100 may turn off to conserve battery power.

One or more of the controllers described herein may include a circuit, a processor, such as a central processing unit (CPU), computer, logic array, or other device capable of directing data coming into or out of the hearing devices described herein. In some embodiments, the controller includes one or more computing devices having memory, processing, and communication hardware. The functions of the controller may be performed by hardware and/or as computer instructions on a non-transient computer readable storage medium.

The processor of the controller may include any one or more of a microprocessor, a controller, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 4:
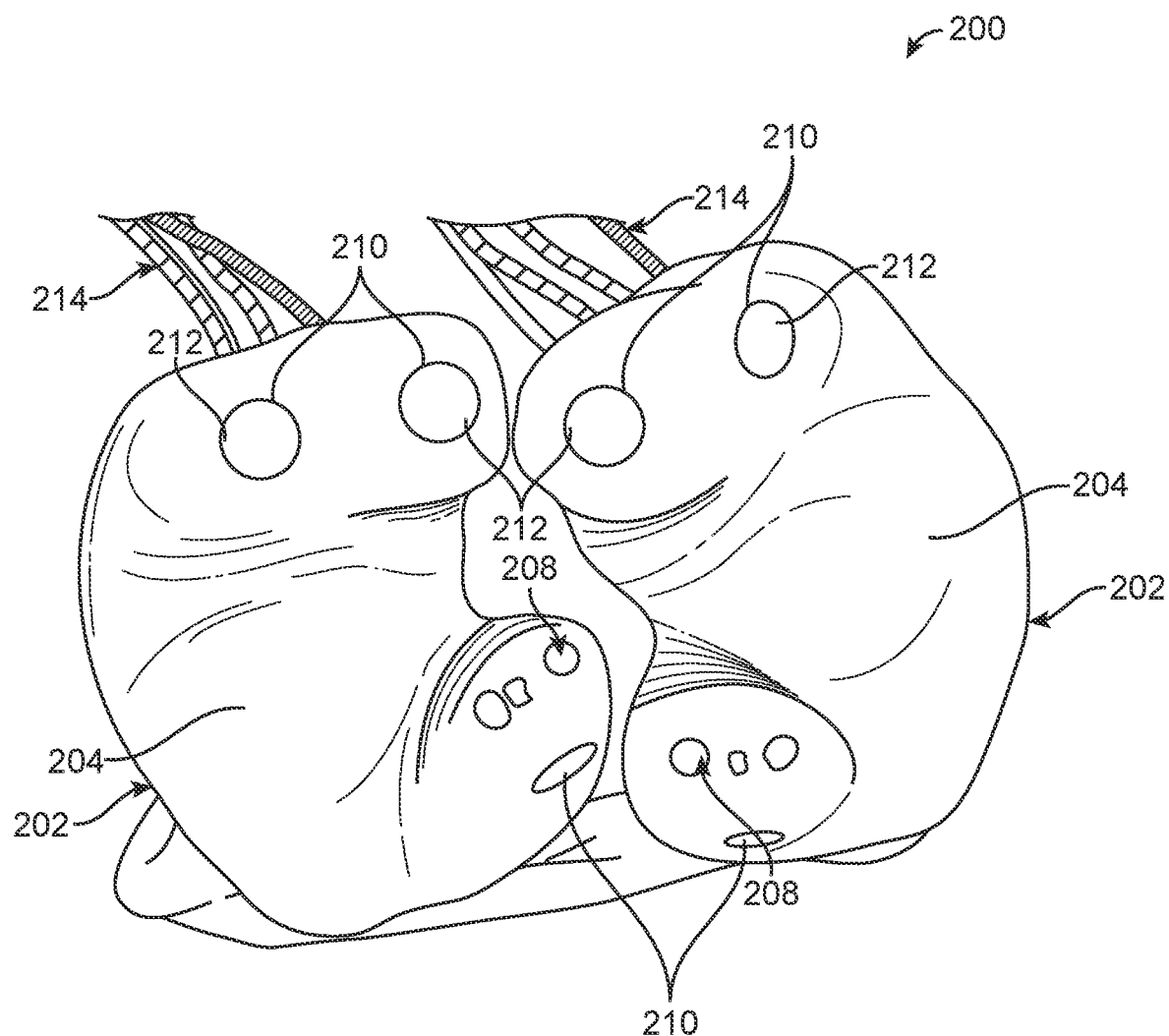
FIG. 4 is an illustration of one embodiment of the hearing device of FIG. 1.
Figure 5A:
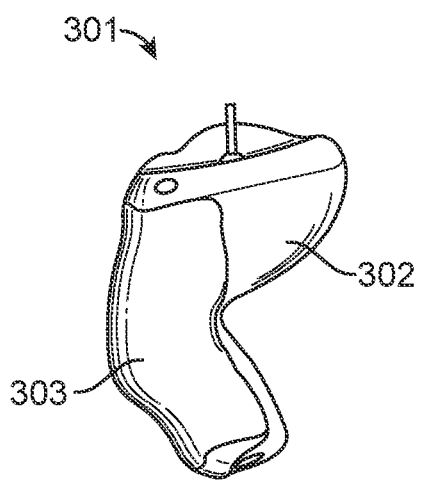
FIGS. 5A, 5B, 5C, and 5D are illustrations of other embodiments of the hearing device of FIG. 1.
Figure 5B:
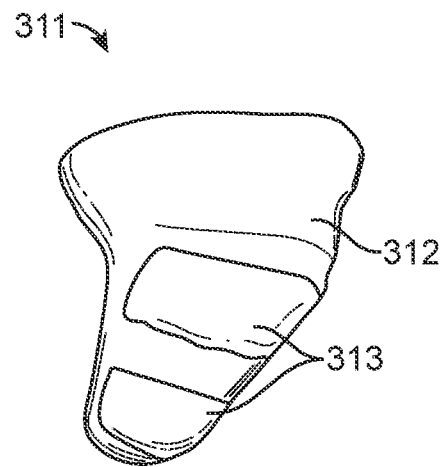
Figure 5C:
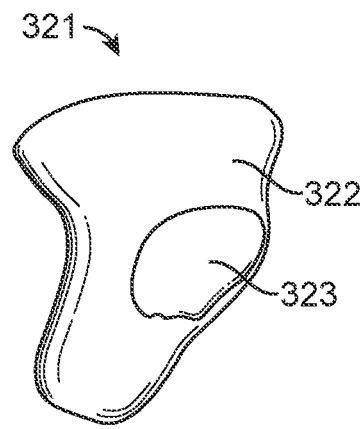
Figure 5D:
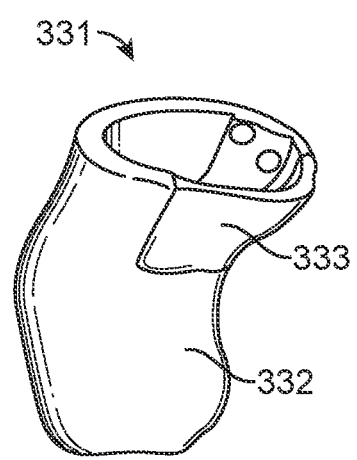

FIG. 4 shows two hearing devices 200 each including a plurality of electrodes 210 formed at least partially or entirely as pellets having conductive material. In the illustrated embodiment, the hearing device 200 includes a body 202 having a housing 204. Further, the electrodes 210 are disposed flush with the housing 204. In particular, the outer conductors 212 are disposed in the housing 204 and flush with the housing 204. The hearing devices 200 may be custom formed to fit in the ear canals of an individual.

The outer conductors 212 may be pellets formed of sintered conductive material or plated conductive material. The inner conductors 214 may include conductive wires electrically coupled to the outer conductors 212, for example, by soldering. Acoustic transducers 208 may be disposed in the body 202 (for example, recessed) and directed outwardly toward apertures formed in the housing 204 to provide sound to the ear canal of the user.

In general, the surface area of the electrodes 210 may be made as large as possible relative to the overall size of the hearing device 200 to facilitate better electrical contact and a lower SNR. In some embodiments, the electrode 210 may cover the entire hearing device 200 or at least portions of the device meant to contact the skin of the user. Some devices 200 include two or more electrodes 210. The use of two or more electrodes 210 may provide the ability to measure properties of electrical signals, for example, by detecting the delay between in electrical signals received at each electrode or by detecting the differential between electrodes. In general, the distance between the electrodes 210 may be made as large as possible relative to the size of the hearing device 200 to facilitate detecting the delay or differences between the signals. Furthermore, placement of the electrode or electrodes 210 may facilitate better measurements for certain applications. In some embodiments having two or more electrodes, one electrode 210 may be placed in the ear canal and another electrode may be placed outside of the ear canal, for example, behind the ear. In general, the electrodes 210 may be used for any application wherein measuring an electrical signal conducted through the skin may be beneficial.

In some embodiments, the electrodes 210 each may be sized to cover less than or equal to about all, about one half, about one fourth, about one eighth, or about one tenth of the outer surface of the respective hearing device 200. In some embodiments, the electrodes 210 may be spaced greater than or equal to about one tenth, about one eighth, about one fourth, about one third, or about one half of a maximum dimension (for example, length) of the hearing device 200.

FIG. 5A, FIG. 5B, FIG. 5C, and FIG. 5D each show various hearing devices 301, 311, 321, 331 having elastomeric conductors. Each of the hearing devices 301, 311, 321, 331 may be custom formed to fit in the ear canal of a particular individual. In the illustrated embodiment, each of the electrodes 303, 313, 323, 333 are disposed flush with the respective housing 302, 312, 322, 332. The electrodes 303, 313, 323, 333 may be formed of conductive material embedded in an elastomer.

The electrodes 303, 313, 323, 333 may be any suitable size to facilitate good electrical contact and the ability to measure a variety of electrical signals. For example, as shown, the electrode 303 may be sized to substantially cover at least about one half of the outer surface of the hearing device 301. As another example, both of the two electrodes 313 together may be sized to substantially cover at least about one quarter of the outer surface of the hearing device 311 while being spaced at least one fourth of the maximum dimension (for example, length) of the hearing device. As a further example, electrode 323 and electrode 333 each may be sized to cover about at least one eighth of the outer surface of the respective hearing device 321, 331.

In some embodiments, to custom fit a hearing device for an individual's ear canal, the ear canal may be measured, for example, by a molding process. The hearing device, particularly the housing, may be made based on those measurements.

Any suitable technique to form a housing may be used. At least one non-limiting example of a technique to form a housing is described in U.S. application Ser. No. 15/429,898, filed Feb. 10, 2017, entitled HEARING ASSISTANCE DEVICE, which is incorporated entirely herein. Various techniques for forming a housing including a conductor for an electrode are described further herein with respect to FIG. 6 and FIG. 7.

Figure 6:
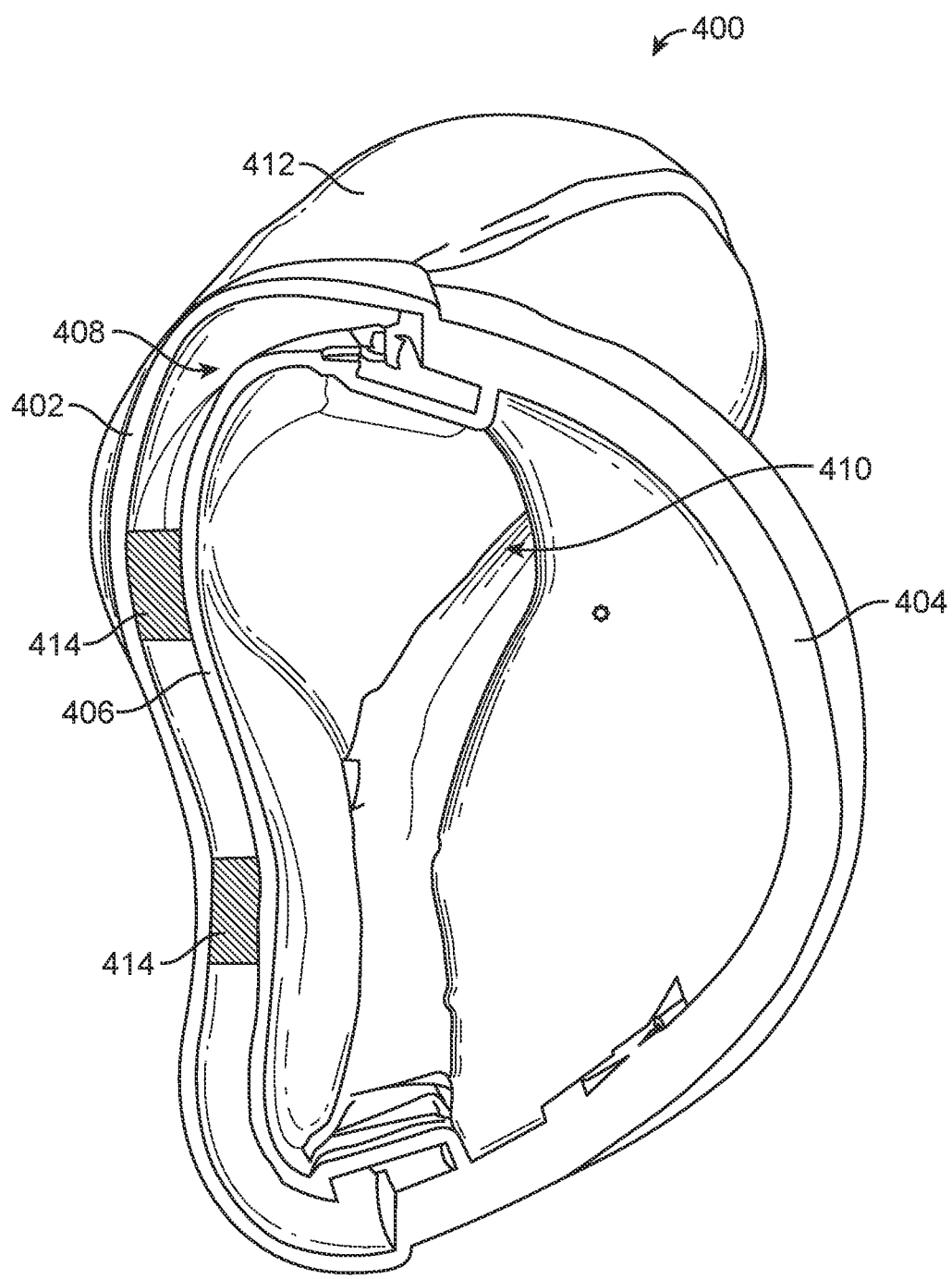
FIG. 6 is an illustration of a cast shell used in forming a housing, according to one technique, for use in the hearing device of FIG. 1.

FIG. 6 shows a cast shell 400 used in forming a housing of a hearing device. The cast shell 400 provided may have a thin outer wall 402, a thick outer wall 404, and an inner wall 406 between the thin and thick outer walls. The cast shell 400 may be formed by any suitable technique, such as injection molding or an additive manufacturing process. A cavity 408 may be disposed proximate to the thin outer wall 402. The cavity 408 may be separated from a void 410 by the inner wall 406. The void 410 may be proximate to the thick outer wall 404. In some embodiments, the thin outer wall 402 may have a thickness that is less than or equal to about 20 mils, about 16 mils, about 12 mils, about 8 mils, about 6 mils, about 4 mils, or less.

An elastomeric conductor 414 may be formed in the cavity 408 of the cast shell 400. The elastomeric conductor 414 may be formed of by any suitable technique, such as injection molding or an additive manufacturing process. In some embodiments, one or more elastomeric conductors 414 may be formed in one or more discrete subcavities, respectively, in the cavity 408. Subcavities may be separated by additional walls of the cast shell 400 or may be defined by a difference in materials formed in the cavity. As shown, two discrete pieces of the elastomeric conductor 414 may be formed in the cavity 408. Another elastomer may be formed in the remainder of the cavity 408, such as an elastomeric conductor or an elastomeric insulator. Using subcavities may facilitate the formation of a small electrode or a plurality of electrodes on a single hearing device for various applications (see, for example, FIG. 5A to 5D). However, in some embodiments, one or more elastomeric conductors 414 may fill almost all or the entire cavity 408.

The thin outer wall 402 may be removed from the remainder of the cast shell 400 to form an outer surface 412 defined at least partially by the thick outer wall 404 and the elastomer that was disposed in the cavity 408, which may include the elastomeric conductor 414. In some embodiments, the outer surface 412 may also be defined by an elastomeric insulator formed in the cavity 408.

Figure 7:
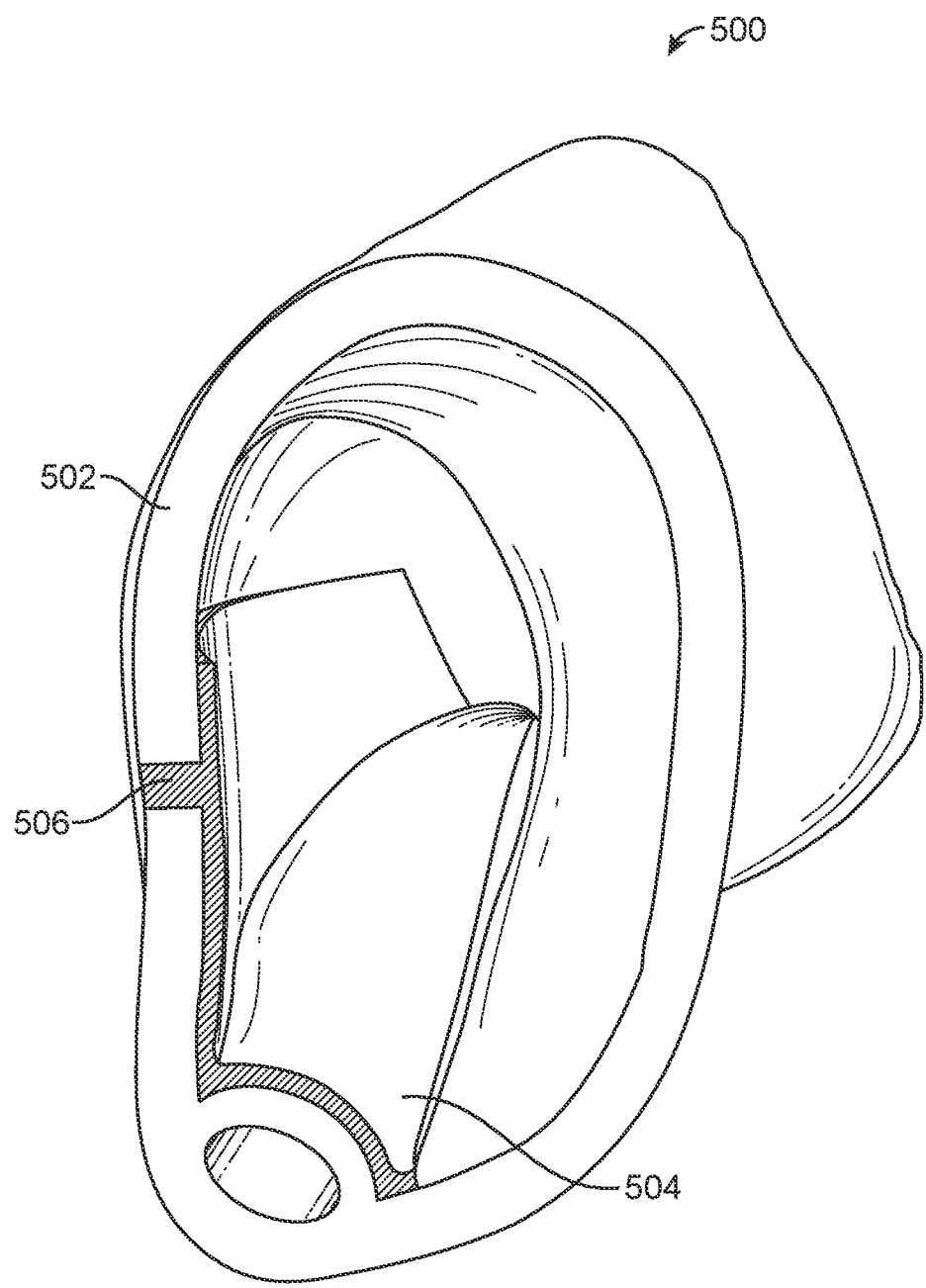
FIG. 7 is an illustration of a housing formed, according to another technique, for use in the hearing device of FIG. 1.

FIG. 7 shows a housing 500 including an electrode 506. The housing 500 may be formed by a shell 502 and a frame 504. The shell 502 and the frame 504 may be formed separately. Although, in some embodiments, the shell 502 and the frame 504 may be formed integrally. In general, the frame 504 may be more rigid than the shell 502. The shell 502 may be formed of a hard or a soft material. In some cases, a soft material may be more comfortable to place in the ear canal.

The frame 504 may be inserted into the shell 502. One or more conductors may extend through the shell 502 to provide one or more electrodes 506. In some embodiments, when the frame 504 includes an electrode 506 prior to insertion, the electrode may puncture through the shell 502 as the frame is inserted. The shell 502 may generally be formed of an electrically insulating material. The frame 504 may be formed of an electrically insulating material. However, the frame 504 may include one or more conductors to electrically couple to the electrode 506.

One or more hearing device components (see FIG. 3) may be disposed on the frame 504. The hearing device components may enable various functionality of the hearing device. A non-limiting example of a hearing device component is a processor. The hearing device components may be operatively coupled to the electrode 506 to enable various functionality using the electrode.

The electrode 506 may be formed in any suitable manner. Non-limiting examples of forming the electrode 506 include one or more of embedding electrically conductive material in the material of the shell 502 and printing or otherwise disposing conductive material on the shell (for example, using 3D printing). In some embodiments, the electrode 506 may be formed with the frame 504. For example, the electrode 506 and frame 504 may be formed by 3D printing. Inserting the shell 502 into the frame 504 may dispose at least part of the electrode 506 through the shell 502. In some embodiments, the electrode 506 may be formed with the shell 502. For example, the electrode 506 and the shell 502 may be formed by cast molding.

Thus, various embodiments of the ELECTRODES FOR HEARING DEVICES AND RELATED METHODS are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements).

Terms related to orientation, such as "interior," "external," and "end" are used to describe relative positions of components and are not meant to limit the orientation of the embodiments contemplated.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The phrases "at least one of," "comprises at least one of," and "one or more of" followed by a list refers to any one of the items in the list and any combination of two or more items in the list.

What is claimed is:

1. A hearing device for electrically coupling to skin of a user, the device comprising:
    a body comprising a housing forming at least part of an outer surface, the body comprising a void defining an interior of the housing;
    a transmitting acoustic transducer configured to transmit sound toward an ear drum of the user, the transmitting acoustic transducer disposed at least partially in the body; and
    an electrode disposed at least partially in the body and configured to contact skin of the user's ear, the electrode configured to sense bioelectric signals and comprising:
        an outer conductor disposed at least partially in the housing and forming at least part of the outer surface, the outer conductor comprising a solid pellet having a coarse or textured skin contact surface and comprising powdered or plated conductive material, the pellet having a cylindrical shape and an axial surface which is coarser or more textured than a radial surface of the pellet; and
        an inner conductor electrically coupled to the outer conductor and extending to or into the void, disposed subflush to the outer surface, and forming at least part of the outer surface; and
    a conductive wire extending through the void and electrically coupled to the inner conductor.

2. The hearing device of claim 1, wherein the powdered conductive material comprises one or more of silver, silver chloride, and silver-silver chloride.

3. The hearing device of claim 1, wherein the powdered conductive material comprises one or more of titanium or titanium nitride.

4. The hearing device of claim 1, further comprising a plurality of electrodes including the electrode.

5. The hearing device of claim 1, wherein the outer conductor is disposed flush to the housing of the body to electrically couple to skin of the user.

6. The hearing device of claim 1, wherein the outer conductor is removably coupled to the inner conductor.

7. The hearing device of claim 1, wherein the outer conductor comprises a microtextured or micropatterned outer surface.

8. A hearing device for electrically coupling to skin of a user, the device comprising:

a body comprising a housing forming at least part of an outer surface, the body comprising a void defining an interior of the housing;

a transmitting acoustic transducer configured to transmit sound toward an ear drum of the user, the transmitting acoustic transducer disposed at least partially in the body; and a plurality of electrodes disposed at least partially in the body and configured to contact skin of the user's ear, each of the electrodes configured to sense bioelectric signals and comprising:

an outer conductor disposed flush or superflush to the housing of the body and forming at least part of the outer surface, the outer conductor comprising a solid pellet having a coarse or textured skin contact surface and comprising powdered or plated conductive material, the pellet having a cylindrical shape and an axial surface which is coarser or more textured than a radial surface of the pellet; and an inner conductor electrically coupled to the outer conductor and extending to or into the void, disposed subflush to the outer surface, and forming at least part of the outer surface; and a conductive wire extending through the void and electrically coupled to the inner conductor.

9. The hearing device of claim 8, wherein the outer conductor comprises a microtextured or micropatterned outer surface.

10. The hearing device of claim 1, wherein the outer conductor is disposed flush to the housing of the body.

11. The hearing device of claim 1, wherein the outer conductor is disposed superflush to the housing of the body.

12. The hearing device of claim 1, wherein the pellet is formed of sintered conductive material.

13. The hearing device of claim 1, wherein the pellet is formed of plated conductive material.

14. The hearing device of claim 1, wherein the inner conductor comprises a conductive wire electrically coupled to the outer conductor.

15. The hearing device of claim 8, wherein the outer conductor is disposed flush to the housing of the body.

16. The hearing device of claim 8, wherein the outer conductor is disposed superflush to the housing of the body.

17. The hearing device of claim 8, wherein the pellet is formed of sintered conductive material.

18. The hearing device of claim 8, wherein the pellet is formed of plated conductive material.

19. The hearing device of claim 8, wherein the inner conductor comprises a conductive wire electrically coupled to the outer conductor.

\* \* \* \* \*